United States Patent [19]

Bertelo et al.

[11] Patent Number: 6,156,832
[45] Date of Patent: Dec. 5, 2000

[54] COMPOSITION BASED ON ORGANOTIN MALEATES WHICH CAN BE USED TO STABILIZE AND LUBRICATE THERMOPLASTIC POLYMERS, PROCESS FOR PRODUCING THE SAID COMPOSITION

[75] Inventors: Chris Bertelo, Scotch Plains, N.J.; Muriel Cuilleret, Lyons, France; Stephane Girois, Jeffersonville, Pa.; Patrick Morel, Ecully, France

[73] Assignees: Elf Atochem North American, Inc., Philadelphia, Pa.; Elf Atochem S.A., Puteax, France

[21] Appl. No.: 09/004,866

[22] Filed: Jan. 9, 1998

[30] Foreign Application Priority Data

Jan. 9, 1997 [FR] France .................................. 97 00147

[51] Int. Cl.$^7$ ....................................................... C08K 3/18

[52] U.S. Cl. ............................ 524/178; 524/567; 556/92; 556/94; 556/90

[58] Field of Search .................................... 524/178, 567; 556/90, 94, 92

[56] References Cited

U.S. PATENT DOCUMENTS

| | | | |
|---|---|---|---|
| 2,454,274 | 11/1948 | Daly et al. | 560/112 |
| 3,555,060 | 1/1971 | Hoch | 556/83 |
| 4,000,100 | 12/1976 | Baldyga | 524/147 |
| 4,231,949 | 11/1980 | Caprini et al. | 556/92 |
| 4,237,043 | 12/1980 | Korbanka et al. | 260/45.75 |

FOREIGN PATENT DOCUMENTS 1270922  4/1972  United Kingdom .

*Primary Examiner*—Robert Dawson
*Assistant Examiner*—Kuo-Liang Peng
*Attorney, Agent, or Firm*—Millen, White, Zelano & Branigan, P.C.

[57] ABSTRACT

The invention relates to a composition containing organotin maleates such as is obtained by reacting a mixture of a low molecular weight alcohol or epoxyalkane and of a high molecular weight alcohol or epoxyalkane with maleic anhydride and by then bringing the mixture thus obtained into contact with a dialkyltin oxide. The invention also relates to poly(vinyl chloride) (PVC) composition stabilized and lubricated using the said composition based on organotin maleates and also to the extruded rigid objects formed from the said PVC compositions.

51 Claims, No Drawings

COMPOSITION BASED ON ORGANOTIN MALEATES WHICH CAN BE USED TO STABILIZE AND LUBRICATE THERMOPLASTIC POLYMERS, PROCESS FOR PRODUCING THE SAID COMPOSITION

CROSS-REFERENCE TO RELATED APPLICATION

This application is related to the following concurrently filed application: entitled "Composition Based on High Molecular Weight Organotin Maleates Which Can Be Used to Stabilize Thermoplastic Polymers. Process for Producing the Said Composition" by Cuilleret, Moreal, Reilly, and Schipper, based on French Priority Application 97/00146 filed Jan. 9, 1997.

FIELD OF THE INVENTION

The subject of the present invention is a composition composed of organotin maleates and a process for the production thereof.

The invention also relates to thermoplastic polymer compositions stabilized and lubricated using the said composition based on organotin maleates. More particularly, the invention relates to vinyl chloride polymer compositions of controlled melting which are stabilized and lubricated using the said composition based on organotin maleates.

A further subject of the invention relates to extruded rigid articles obtained from vinyl chloride polymer compositions of controlled melting which are stabilized and lubricated using the said composition based on organotin maleates.

BACKGROUND OF THE INVENTION

A number of organotin maleates forming good heat-stabilization and photostabilization agents for vinyl chloride polymers are known.

Thus, compositions containing organotin maleates, such a dibutylin bis(isooctyl maleate) or dibutylin bis(isooctyl maleate) oxide, are described in the literature. The use of these compositions as heat-stabilizers for halogenated organic compounds, in particular halogenated polymers such as poly(vinyl chloride) (PVC) and chlorinated poly (vinyl chloride) (CPVC), is also well known.

The effectiveness of stabilizers based on organotin maleate for PVC, in particular articles intended for external use, is well known.

Thus, in the article entitled "Worldwide Weathering of Polyvinyl Chloride", by Emery Szabo and Robert Lally; Polymer and Engineering Science, April 1975, Vol. 15, No. 4, the results of studies on long-term exposure to weather are presented. The stabilizing compositions used were compositions containing barium/cadmium soaps, compositions containing organotin maleates and compositions containing organotin mercaptoacetates. It is noted, in the conclusions, that DBTM (dibutyltin maleate) gives the best results as UV stabilizer and that organotin mercaptoacetates give the worst results.

Although the superiority of compositions containing organotin maleates in the stabilization of PVC formulations subjected to weathering has been recognized for a long time, these compositions have not succeeded in fully satisfying market requirements because of many disadvantages.

Thus, British Patent 787,930 explains, from page 1, line 65 to page 2, line 3, that dibutyltin maleate is difficult to disperse and in addition generates, during the conversion of PVC, a volatile maleic anhydride fraction which has lacrimatory and irritating effects on the people handling it. In order to overcome these faults, GB 787,930 provides compositions containing organotin maleate hemiesters which are liquid, such as dibutyltin bis(monobutyl maleate). The presence of the alcohol group of the ester has the effect of decreasing the tin content, causing reduced heat stabilization, but does not remove the volatile fraction generated by the stabilization mechanism, that is to say the formation of the hemiester of maleic acid by the reaction of organotin bis(monoalkyl maleate) with the gaseous HCl generated during the processing of PVC.

U.S. Pat. No. 3,296,289 describes stabilizing compositions containing diorganotin maleate hemiester which are improved insofar as these compositions, composed of diorganotin bis(maleate hemiesters), are solid at room temperature. A typical composition from U.S. Pat. No. 3,296,289 was dibutyltin bis(cyclohexyl maleate), having a melting point of 71° C. to 73° C., as described in Example 1. Although the solid compositions containing organotin maleate hemiester described in U.S. Pat. No. 3,296,289 make it possible to solve some handling problems, they do not for all that remove the irritating volatile compounds generated when the stabilizing compositions are subjected to the heat conditions applied during the processing of PVC, which is carried out at approximately 200° C.

U.S. Pat. No. 3,555,060 relates to organic tin compounds, such as, in particular, dibutyltin bis(isooctyl maleate).

These compounds are complex chelates exhibiting an $\equiv$Sn—O—Sn$\equiv$ bond with 2 tin atoms per molecule.

However, these products are viscous, coloured liquids which are difficult to use.

Another problem which is raised by the use of organotin maleates as heat-stabilizer for vinyl chloride polymers is the difficulty of processing these formulations. Indeed, it is well known, in particular during the extrusion of rigid PVC, that the molten polymer containing the said stabilizers exhibits a strong tendency to adhere to the conversion equipment.

To overcome this problem, use is made of sometimes complex combinations of lubricants and attempts are more rarely made to modify the structure of the stabilizer itself.

Thus, Patent GB 1,378,851 provides for the addition of a mixture of paraffin wax and of a lubricating acrylic polymer to a PVC formulation containing dibutyltin di(methyl maleate), so as to reduce the adhesion to the equipment. The improvement thus obtained is characterized by a greater ease in detaching a film converted on a roll mill but, however, remains unsatisfactory.

However, the significant, indeed excessive, addition of lubricants to PVC formulations can have disadvantages. Thus, an excessively high content of internal lubricant will have, inter alia, consequences of increasing the plasticization of the PVC and thus of decreasing its Vicat point. In the case of rigid formulations, this can be a factor which prohibits the use of organotin maleates.

In the same way, an excess of external lubricant, intended to limit problems of adhesion during extrusion, will have a tendency to promote phenomena of exudation and thus of deposits on the equipment.

Thus, despite more than thirty years of research, heat-stabilizers for PVC based on organotin maleates continue to have a limited use although they exhibit excellent stabilizing properties and very good resistance to weathering. Their properties cannot be regarded as entirely satisfactory:

either because, during processing, they decompose to give volatile products which are irritating and lacrimatory, or because they are difficult to process.

SUMMARY OF THE INVENTION

A composition containing organotin maleates has now been found which can be obtained by reacting, optionally in solvent medium and/or in the presence of water, a mixture composed of at least one component RA and at least one component $R^1A$ with maleic anhydride or maleic acid and by then bringing the reaction mixture thus obtained into contact with at least one dialkyltin oxide $(R^2)_2Sn=O$ or at least one alkyltin chloride $(R^2)_xSnCl_{4-x}$, given that:

RA represents
  either an alcohol ROH in which R represents a linear or branched aliphatic hydrocarbon radical having a number of carbon atoms ranging from 1 to 10 and preferably of between 5 and 8 or a mixture of alcohols with a weight-average molecular mass $\overline{Mw}$ greater than 32 and not more than 158,
  or an epoxyalkane $C_nH_{2n}O$ in which n ranges from 1 to 10 or a mixture of epoxyalkanes with a weight-average molecular mass Mw greater than 30 and not more than 156;

$R^1A$ represents
  either an alcohol $R^1OH$ in which $R^1$ represents a linear or branched aliphatic hydrocarbon radical having a number of carbon atoms ranging from 20 to 50 or a mixture of saturated primary alcohols with a weight-average molecular mass $\overline{Mw}$ ranging from 298 to 718,
  or an epoxyalkane $C_pH_{2p}O$ in which p ranges from 20 to 50 or a mixture of epoxyalkanes with a weight-average molecular mass $\overline{Mw}$ ranging from 296 to 716;

$R^2$ represents a linear or branched aliphatic hydrocarbon radical having a number of carbon atoms ranging from 1 to 12 and preferably equal to 1, 4 or 8, x is an integer equal to 1 or 2.

The thermoplastic polymer in which the composition based on organotin maleates can be incorporated for the purpose of improving, in particular, the heat stability and the light stability thereof can in particular consist of one or more addition polymers chosen from the group formed by vinyl chloride homopolymers which can optionally be overchlorinated and the copolymers, optionally grafted, which result from the copolymerization of vinyl chloride with one or more ethylenically unsaturated comonomers. The following are in particular suitable as comonomers for the preparation of such copolymers: vinylidene halides, such as vinylidene chloride or fluoride, vinyl carboxylates, such as vinyl acetate, vinyl propionate or vinyl butyrate, acrylic and methacrylic acids and the nitrites, amides and alkyl esters which derive therefrom, in particular acrylonitrile, acrylamide, methacrylamide, methyl methacrylate, methyl acrylate, butyl acrylate, ethyl acrylate or 2-ethylhexyl acrylate, vinylaromatic derivatives, such as styrene or vinylnaphthalene, or olefins, such as bicyclo[2.2.1] hept-2-ene, bicyclo[2.2.1] hepta-2,5-diene, ethylene, propylene or 1-butene.

The invention very particularly relates, among these polymers, to homo- and copolymers of vinyl chloride which are optionally overchlorinated.

The composition based on organotin maleates according to the present invention can be prepared according to the preferred method below, which consists first in producing a homogeneous and liquid mixture of the components RA and $R^1A$ in solvent medium while heating. The mixture obtained is brought to a temperature of at least 50° C. and preferably of between 70° C. and 100° C., maleic anhydride is then first added, continuously or portionwise, over a period of time which can range from 15 minutes to approximately 1 hour and then a dialkyltin oxide $(R^2)_2Sn=O$ is subsequently added, continuously or portionwise, over a period of time of at least 15 minutes and preferably ranging from 30 minutes to 90 minutes.

The reaction mixture is then maintained at a temperature ranging from 50° C. to 120° C. and preferably of between 75° C. and 100° C. for a period of time of at least 15 minutes and preferably of between 30 minutes and 90 minutes.

The water formed during the reaction and the solvent can be removed by distillation under reduced pressure at a temperature ranging from 70° C. to 120° C. and preferably of between 80° C. and 100° C.

The solvent used must be inert with respect to the reactants and the products formed.

Mention will be made, by way of illustration of solvents which can be used according to the present invention, of toluene, xylenes, heptane or THF.

According to the present invention, the preparation is carried out with stirring and preferably while bubbling through an inert gas, such as nitrogen.

The preparation is generally carried out at atmospheric pressure ($10^5$ Pa) but it would not be departing from the scope of the invention if the preparation were carried out at a different pressure.

Should epoxyalkanes be used, the preparation will be carried out in the presence of water. The latter can advantageously be introduced before the addition of the maleic anhydride.

According to the present invention, the components RA and $R^1A$, and the maleic anhydride, will be used in a maleic anhydride/(RA+$R^1A$) molar ratio of at least 1.5 and preferably of between 2 and 2.5.

According to the present invention, the ratio of the molar percentages RA/$R^1A$ can vary within wide limits. This ratio can range from 1/99 to 99/1 and preferably between 20/80 and 80/20.

Mention will be made, by way of illustration of components RA which can be used according to the present invention, of alcohols ROH, such as methanol, ethanol, n-propanol, n-butanol, n-pentanol, n-hexanol, 2-ethylhexanol, n-octanol, n-decanol or a mixture of at least two of the abovementioned alcohols; 1,2-epoxyalkanes $C_nH_{2n}O$, such as 1,2-epoxybutane, 1,2-epoxyhexane, 1,2-epoxyoctane, 1,2-epoxydecane or a mixture of at least 2 of the abovementioned epoxyalkanes.

2-Ethylhexanol will preferably be used.

Mention will be made, by way of illustration of components $R^1A$ which can be used according to the present invention, of alcohols $R^1OH$, such as 1-nonacosanol (montanyl alcohol), hentriacontanol, n-triacontanol (myricyl alcohol) or mixtures of saturated primary alcohols having a weight-average molecular mass $\overline{Mw}$ ranging from 375 to 700, a polydispersity $\overline{Mw}/\overline{Mn}$ in the region of 1 ($\overline{Mn}$ representing the number-average molecular mass) and a regular distribution of the linear aliphatic hydrocarbon radicals as a function of the length of the hydrocarbon chains, or mixtures of 1,2-epoxyalkanes having a weight-average molecular mass $\overline{Mw}$ ranging from 313 to 632.

Use will preferably be made of a mixture of saturated primary alcohols having a mass $\overline{Mw}$ of 460 or of a mixture of epoxyalkanes having a mass $\overline{Mw}$ of 632.

According to the present invention, at least 0.50 mol of dialkyltin oxide $(R^2)_2Sn=O$ and preferably an amount ranging from 0.75 mol to 0.85 mol will be used per 1 mol of maleic anhydride.

Mention will be made, by way of illustration of dialkyltin oxides which can be used according to the present invention, of dimethyltin oxide, dibutyltin oxide or dioctyltin oxide.

The use, among these compounds, of dibutyltin oxide is very particularly preferred.

It is also possible to use, during the preparation of the composition based on organotin maleates, at least one alkyltin chloride $(R^2)_xSnCl_{4-x}$ instead of a dialkyltin oxide $(R^2)_2Sn=O$.

Use will preferably be made of a mixture of monoalkyltin trichloride $R^2SnCl_3$ and of dialkyltin dichloride $(R^2)_2SnCl_2$, it being possible for the radicals $R^2$ of the trichloride and of the dichloride to be identical or different.

In this case, the chlorides formed during the preparation of the composition can be neutralized with an alkaline hydroxide.

The composition based on organotin maleates according to the present invention has a tin content by weight of at least 10% and preferably of between 15% and 25%.

In the general case where the compositions obtained are solid at room temperature, the latter can be isolated by means known to a person skilled in the art, such as, in particular, by pouring the hot liquid reaction mixture onto a cooled surface and then flaking the solidified product.

It would not be departing from the scope of the invention if the composition containing organotin maleates was obtained by separately preparing two compositions containing organotin maleates which respectively contain low molecular weight components RA and high molecular weight components $R^1A$ and by then subsequently mixing them.

The tin content of the composition obtained can be determined by elemental analysis. The infrared spectrum of the composition according to the invention is characterized by:

- an absorption band in the region of 1730 cm$^{-1}$ characteristic of ester functional groups,
- an absorption band in the region of 1580 cm$^{-1}$ characteristic of tin carboxylates,
- an absorption band in the region of 680 cm$^{-1}$ characteristic of $\equiv$Sn—O—Sn$\equiv$ bonds.

The composition based on organotin maleates can be obtained according to an alternative form which consists in introducing, after the removal of the water formed and optionally of the solvent, an amount of costabilizer of at least 10% by weight and preferably of between 15% and 30%, with respect to the reactants employed (excluding water).

Having carried out this addition, the reaction mixture is kept stirred and heated until a homogeneous mixture is obtained.

Mention will be made, by way of illustration of costabilizers which can be used according to the present invention, of zeolites, hydrotalcites or calcium and zinc salts of fatty acids.

Another subject of the invention is a process for producing organotin maleates, characterized in that a mixture composed of at least one component RA and at least one component $R^1A$ is reacted with maleic anhydride and that the reaction mixture thus obtained is then brought into contact with at least one dialkyltin oxide $(R^2)_2Sn=O$ or with at least one alkyltin chloride $(R^2)_xSnCl_{4-x}$.

RA, $R^1A$, $(R^2)_2Sn=O$ and $(R^2)_xSnCl_{4-x}$ have the same meaning as given above. The operating conditions and parameters, the reactants used and their proportions are as defined above.

The invention also relates to compositions comprising the thermoplastic polymer and the composition based on organotin maleates as they have been defined above.

The composition based on organotin maleates can be used in amounts ranging from 0.5 to 5 parts by weight, preferably from 1 to 4 parts, per 100 parts by weight of thermoplastic polymer.

Such compositions can additionally contain, as a function in particular of the processing or conversion conditions and/or of the applications for which they are intended, the usual additives, such as pigments, fillers, lubricants, processing aids, impact modifiers, antioxidants, plasticizers and blowing agents.

The composition based on tin as obtained according to the present invention can be incorporated at the same time as or before the additives mentioned above, when they are made use of.

According to a particularly recommended form, this operation is carried out in a fast mixer and the thermoplastic polymer, the composition based on organotin maleates and then the additives and the fillers are successively introduced.

As a general rule, this operation can be carried out at room temperature, it being possible for the operation itself to cause a temperature rise up to 70° C., indeed more.

The stabilizing action of the composition based on organotin maleates as obtained according to the present invention can be demonstrated by carrying out various tests which evaluate the dynamic and static thermal stability of thermoplastic polymer compositions containing it.

Thermoplastic polymer compositions, in particular PVC compositions, comprising the composition based on organotin maleates as obtained according to the present invention can be moulded by injection, calendered and then thermoformed, extruded or coextruded as rigid articles, such as interior coverings for buildings, door frames, window sections, sheets and pipes. The converted articles can be compact or expanded.

The heat- and light-stabilizing action of the composition based on organotin maleates can be demonstrated for the converted articles by measurement of the trichromaticity coordinates L*, a* and b*, by measurement of the residual stability time by a Congo Red test and by subjecting these articles to UV radiation.

The composition containing organotin maleates as obtained according to the present invention exhibits the advantages, in addition to heat stabilizing thermoplastic polymer compositions containing it, of controlling the gelling and the lubrication thereof.

The composition containing organotin maleates of the present invention makes it possible in particular to obtain controlled melting of thermoplastic polymer compositions containing it, this being obtained by varying the nature, the ratio and the total amount of the various reactants and more particularly of the components RA and $R^1A$.

It has been observed that the high molecular weight components $R^1A$ contribute a lubricating effect to thermoplastic polymer compositions, whereas the low molecular weight components RA make it possible to promote gelling and to control the melting time. These characteristics can be demonstrated by studying the rheology of thermoplastic polymer compositions using a torsional couple rheometer or by reading the conversion parameters during processing. It has thus been found that the lubricating effect contributed by the presence of high molecular weight component $R^1A$ in the composition containing organotin maleates makes it possible to significantly reduce the addition of lubricant to thermoplastic polymer compositions.

The composition containing organotin maleates as obtained according to the present invention also has the advantage of not detrimentally affecting the Vicat point of converted thermoplastic polymer compositions.

Moreover, during the conversion of thermoplastic polymer compositions containing the said composition containing organotin maleates, and more particularly by extrusion, no release of irritating products is observed.

It has also been observed that the use of the components RA and R$^1$A during the preparation of the composition containing organotin maleates according to the present invention made it possible to reduce, indeed eliminate, the formation of deposits on the equipment used for the conversion of thermoplastic polymer compositions containing the said composition containing organotin maleates.

The following examples illustrate the invention.

I Preparation of compositions containing organotin maleates in accordance with the invention The compositions containing organotin maleates were prepared by using the following reactants:

Unilin® 425 (sold by the Company Petrolite): mixture of saturated primary alcohols having a weight-average molecular mass $\overline{Mw}$ of 460, a polydispersity $\overline{Mw}/\overline{Mn}$ of 1, a melting point of 91° C., a hydroxyl number of 105 mg KOH/g of sample determined according to ASTM Standard D 222 and a mean number of carbon atoms of 30;

Unilin® 550 (sold by the Company Petrolite):

mixture of saturated primary alcohols having a weight-average molecular mass $\overline{Mw}$ of 550, a polydispersity $\overline{Mw}/\overline{Mn}$ of 1, a melting point of 99° C., a hydroxyl number of 83 mg KOH/g of sample determined according to ASTM Standard D 222 and a mean number of carbon atoms of 40;

Vikolox® C30+ (sold by the company Elf Atochem North America Inc.): mixture of 1,2-epoxyalkanes having a weight-average molecular mass $\overline{Mw}$ of 632 and exhibiting a melting point of 72.7° C. and a mean number of carbon atoms of 45;

Valfor® 100 (sold by the company The PQ Corporation): Zeolite A of sodium aluminosilicate hydrate type;

2-ethylhexanol, maleic anhydride, dibutyltin oxide.

EXAMPLE 1

PREPARATION OF A COMPOSITION CONTAINING ORGANOTIN MALEATES ACCORDING TO THE INVENTION IN SOLVENT MEDIUM

The following are introduced into a 500 ml jacketed reactor equipped with a stirrer, a thermometer pocket, a reflux condenser equipped with a Dean and Stark apparatus, and an inert gas inlet:

100 ml of heptane (solvent), 84.2 g (0.183 mol) of Unilin® 425, 5.9 g (0.045 mol) of 2-ethylhexanol, i.e. a ratio of the 2-ethylhexanol/Unilin® 425 molar percentages of 20/80.

The mixture is heated to approximately 85° C. and stirred so as to obtain a homogeneous, liquid reaction mixture. 53.6 g (0.546 mol) of maleic anhydride are introduced in four portions over 30 minutes under a stream of nitrogen, causing a slight exotherm to 95° C. When the temperature again stabilizes at approximately 85° C., 109.5 g (0.440 mol) of dibutyltin oxide are added in five portions over 1 hour. The reaction mixture is maintained with stirring under a stream of nitrogen for 1 hour at 85° C. The temperature is raised by 5° C. to 10° C. before applying a pressure of 6.66×10$^3$ Pa in order to distil off the heptane and the water of reaction (approximately 2 g of water). After distilling for 1 hour, the reactor is returned to atmospheric pressure. Heating and stirring are halted and the reaction mixture is poured onto a cooled metal plate, so as to solidify it.

Approximately 248 g of the composition are obtained, i.e. a yield by weight in the region of 99%. The percentage by weight of tin in the composition thus obtained is 20.8%. The infrared spectrum exhibits an absorption band at 1729 cm$^{-1}$ corresponding to the ester functional groups, an absorption band at 1579 cm$^{-1}$ corresponding to the tin carboxylate functional groups —C(O)—O—Sn≡ and an absorption band at 680 cm$^{-1}$ characteristic of ≡Sn—O—Sn≡ bonds.

EXAMPLE 2

PREPARATION OF A COMPOSITION CONTAINING ORGANOTIN MALEATES ACCORDING TO THE INVENTION USING A ZEOLITE AS COSTABILIZER

The preparation is carried out as in Example 1, using the same reactants but according to different amounts. The following are thus introduced:

100 ml of heptane (solvent), 79.7 g (0.173 mol) of Unilin® 425, 10.4 g (0.079 mol) of 2-ethylhexanol, i.e. a ratio of the 2-ethylhexanol/Unilin® 425 molar percentages of approximately 30/70, 53.6 g (0.546 mol) of maleic anhydride, 109.5 g (0.440 mol) of dibutyltin oxide.

After the removal of the heptane and the water of reaction by distillation under reduced pressure, the reactor is returned to atmospheric pressure and 64 g of Valfor® 100 are introduced in four portions over 30 minutes with stirring while maintaining the temperature at 85° C. After homogenizing the reaction mixture, the product is isolated as in Example 1.

Approximately 315 g of the composition are obtained, i.e. a yield by weight in the region of 100%. The percentage by weight of tin in the composition thus obtained is 16.6%. The infrared spectrum exhibits bands similar to those of the composition of Example 1.

EXAMPLE 3

PREPARATION OF A COMPOSITION ACCORDING TO THE INVENTION USING A MIXTURE OF 1,2-EPOXYALKANES IN THE PRESENCE OF WATER AND IN THE ABSENCE OF SOLVENT

The preparation is carried out according to the operating conditions of Example 1, in an identical reactor, with the following amounts of reactants:

25 g of water, 79.7 g (0.126 mol) of Vikolox® C30+, 10.4 g (0.079 mol) of 2-ethylhexanol, i.e. a ratio of the 2-ethylhexanol/Vikolox® C30+ molar percentages of approximately 40/60, 53.6 g (0.546 mol) of maleic anhydride, 109.5 g (0.440 mol) of dibutyltin oxide.

Distillation under reduced pressure is carried out similarly to Example 1 and 22 g of water are collected after 1 hour. 64 g of Valfor® 100 are then introduced into the reaction mixture as described in Example 2.

The product is collected as in Examples 1 and 2. Approximately 319 g of the composition are obtained, i.e. a yield by weight in the region of 100%. The percentage by weight of tin in the composition thus obtained is 16.4%.

The infrared spectrum exhibits an absorption band at 1736 $cm^{-1}$ corresponding to the ester functional groups, an absorption band at 1581 $cm^{-1}$ corresponding to the tin carboxylate functional groups —C(O)—O—Sn≡ and an absorption band at 681 $cm^{-1}$ characteristic of ≡Sn—O—Sn≡ bonds.

EXAMPLE 4

PREPARATION OF A COMPOSITION ACCORDING TO THE INVENTION USING A MIXTURE OF 1, 2-EPOXYALKANES IN THE PRESENCE OF WATER AND IN THE ABSENCE OF SOLVENT

The preparation is carried out as in Example 3, using the same reactants but according to different amounts. The following are thus introduced:

25 g of water, 74.6 g (0.118 mol) of Vikolox® C30+, 15.4 g (0.118 mol) of 2-ethylhexanol, i.e a ratio of the 2-ethylhexanol/Vikolox® C30+ molar percentages of 50/50, 53.6 g (0.546 mol) of maleic anhydride, 109.5 g (0.440 mol) of dibutyltin oxide.

Distillation under reduced pressure is carried out similarly to Example 1 and 23 g of water are collected after 1 hour. 64 g of Valfor® 100 are then introduced into the reaction mixture as described in Example 2.

The product is collected as in Examples 1, 2 and 3. Approximately 319 g of the composition are obtained, i.e. a yield by weight in the region of 100%. The percentage by weight of tin in the composition thus obtained is 16.4%. The infrared spectrum exhibits absorption bands similar to those of Example 3.

EXAMPLE 5

PREPARATION OF A COMPOSITION ACCORDING TO THE INVENTION SIMILAR TO EXAMPLE 2 WITH VARIATION IN THE RATIO OF THE 2-ETHYLHEXANOL/UNILIN® 425 MOLAR PERCENTAGES

The preparation is carried out as in Example 2, using the same reactants but according to different amounts. The following are thus introduced:

100 ml of heptane (solvent), 87.3 g (0.190 mol) of Unilin® 425, 2.8 g (0.022 mol) of 2-ethylhexanol, i.e. a ratio of the 2-ethylhexanol/Unilin® 425 molar percentages of 10/90, 53.6 g (0.546 mol) of maleic anhydride, 109.5 g (0.440 mol) of dibutyltin oxide.

After the distillation under reduced pressure of the heptane and the water formed, 64 g of Valfor® 100 are introduced, as in Example 2.

Approximately 315 g of the composition are obtained, i.e. a yield by weight in the region of 100%. The percentage by weight of tin in the composition thus obtained is 16.6%. The infrared spectrum exhibits absorption bands similar to those of the composition of Example 2.

EXAMPLE 6

PREPARATION OF A COMPOSITION ACCORDING TO THE INVENTION SIMILAR TO EXAMPLE 2 WITH VARIATION IN THE RATIO OF THE 2-ETHYLHEXANOL/UNILIN® 425 MOLAR PERCENTAGES

The preparation is carried out as in Example 2, using the same reactants but according to different amounts. The following are thus introduced:

100 ml of hexane (solvent), 70.2 g (0.153 mol) of Unilin® 425, 19.9 g (0.153 mol) of 2-ethylhexanol, i.e. a ratio of the 2-ethylhexanol/Unilin® 425 molar percentages of 50/50, 53.6 g (0.546 mol) of maleic anhydride, 109.5 g (0.440 mol) of dibutyltin oxide.

After the distillation under reduced pressure of the heptane and the water formed, 64 g of Valfor® 100 are introduced, as in Example 2.

Approximately 314 g of the composition are obtained, i.e. a yield by weight in the region of 100%. The percentage by weight of tin in the composition thus obtained is 16.6%. The infrared spectrum exhibits absorption bands similar to those of the composition of Example 2.

EXAMPLE 7

PREPARATION OF A COMPOSITION ACCORDING TO THE INVENTION USING UNILIN® 550 AS REPLACEMENT FOR UNILIN® 425

The preparation is carried out as in Example 2, using the reactants according to the following amounts:

100 ml of heptane (solvent), 82.5 g (0.150 mol) of Unilin® 550, 8.2 g (0.063 mol) of 2-ethylhexanol, i.e. a ratio of the 2-ethylhexanol/Unilin® 550 molar percentages of 30/70, 53.6 g (0.546 mol) of maleic anhydride, 109.5 g (0.440 mol) of dibutyltin oxide.

After the distillation under reduced pressure of the heptane and the water formed, 64 g of Valfor® 100 are introduced, as in Example 2.

Approximately 315 g of the composition are obtained, i.e. a yield by weight in the region of 100%. The percentage by weight of tin in the composition thus obtained is 16.6%. The infrared spectrum exhibits absorption bands similar to those of the composition of Example 2.

II Preparation of PVC compositions, herein-after denoted by PVC formulations, containing the compositions containing organotin maleates prepared above and evaluation of the stabilizing and rheological properties of the said compositions containing organotin maleates.

The trade names, natures, suppliers and functions of the various materials used in the preparation of the PVC formulations are given below:

Lacovyl S110P, PVC resin with a K value of 67, Elf Atochem S.A.,

Durastrength 300, acrylic polymer, Ceca S.A., impact modifier,

Stavinor CA PSE, calcium stearate, Ceca S.A., lubricant,
Metablen P551, acrylic polymer, Metablen Company B.V., processing aid,
Kronos S2220, titanium oxide, Kronos, pigment,
Hydrocarb 95T, calcium carbonate, Omya S.A., filler,
AC 316, oxidized polyethylene wax, Allied Signal, lubricant.

THE PVC FORMULATIONS ARE PREPARED ACCORDING TO THE FOLLOWING OPERATING CONDITIONS (THE AMOUNTS OF THE MATERIALS USED ARE EXPRESSED BY WEIGHT):

The following is introduced into a Henschel jacketed fast mixer with a stirring speed of 3800 revolutions/minute:

100 parts of PVC resin (Lacovyl S 110 P).

A rise in temperature is observed.

3.5 parts of a composition containing organotin maleates as obtained according to the present invention are introduced at 60° C. and then 0.2 part of oxidized polyethylene wax (AC 316) is introduced at 65° C.

The following are added at 80° C.:

0.6 part of calcium stearate (Stavinor CA PSE), 7.5 parts of impact modifier (Durastrength 300) and, 1 part of processing aid (Metablen P 551).

The following are then added at 85° C.:

4 parts of titanium oxide (Kronos S2220), 5 parts of calcium carbonate (Hydrocarb 95 T).

The PVC formulation is stirred at 3800 revolutions/minute until a temperature of 110° C. is reached and then cooled by reducing the stirring to 1500 revolutions/minute and by circulating a stream of cold water in the jacket of the mixer.

The formulation obtained is collected when the temperature reaches approximately 45° C.

Two PVC formulations as prepared above are evaluated on a Haake-Rheocord 90 rheometer at 185° C. at a speed of 45 revolutions/minute and with a load of 65 g.

The results are reported in Table 1.

The following designations are used in this Table 1:

PVC formulation 1, a formulation containing the compostion containing organotin maleates of Example 3;

PVC formulation 2, a formulation containing the composition containing organotin maleates of Example 4;

Degradation time, the time at the end of which a large rise in the torque is observed, related to crosslinking and thus to complete degradation of the PVC.

TABLE 1

|  | PVC formulation 1 | PVC formulation 2 |
|---|---|---|
| Melting time (min) | 2.00 | 1.33 |
| Torque at melting (N.m) | 18.0 | 21.5 |
| Torque at equilibrium (N.m) | 17.0 | 20.0 |
| Degradation time (min) | 28.0 | 28.0 |

The influence of the molar ratio of the low molecular weight alcohols or epoxides to the high molecular weight alcohols or epoxides on the melting time and the viscosity (expressed by the torque) of the PVC formulation in the molten state is thus demonstrated.

On increasing the amount of low molecular weight alcohol (2-ethylhexanol) with respect to the amount of high molecular weight 1,2-epoxyalkane (Vikolox® C30+), everything otherwise being equal, the melting time is significantly decreased.

Conversely, the increase in the amount of high molecular weight 1,2-epoxyalkane results in a significant decrease in the torque, demonstrating the lubricating effect contributed by the long chains.

The same formulations were converted on a Krauss-Maffei KMDL25 extruder equipped with a 30×3 mm flat dye. The parameters recorded during the extrusion are presented in Table 2:

TABLE 2

|  | PVC formulation 1 | PVC formulation 2 |
|---|---|---|
| Temperature profile (° C.) | 130–180–190–200 | |
| Bulk temperature (° C.) | 190 | 191 |
| Motor speed (rev/min) | 15 | 15 |
| Torque (%) | 24 | 50 |
| Bulk head pressure (bar) | 120 | 134 |
| Throughput (kg/h) | 4.0 | 4.0 |

The following evaluations were carried out on the strips extruded:

Colorimetry (measurement of the trichromaticity coordinates L*, a* and b* and calculation of the yellowing indices (YI) and of the whiteness indices (WI) according to ASTM Standard E313) using a Minolta Chromameter CR200 spectrocolorimeter, Vicat point or softening temperature, measured using an EDT Vicat Tester AFS, Residual stability expressed in minutes, measured using a Liebish Congo Red bench.

The results are presented in Table 3:

TABLE 3

|  | PVC formulation 1 | PVC formulation 2 |
|---|---|---|
| L* | 94.3 | 94.0 |
| a* | −0.74 | −0.71 |
| b* | 2.50 | 2.37 |
| YI | 3.7 | 3.6 |
| WI | 73.0 | 73.1 |
| Vicat Point (° C.) | 79.4 | 79.4 |
| Congo Red (min) | 44 | 40 |

The influence of the ratio of the molar percentages of the low molecular weight alcohols or 1,2-epoxyalkanes to the high molecular weight alcohols or 1,2-epoxyalkanes on the lubrication of the PVC formulation is again demonstrated, as shown by the torque and bulk pressure values obtained (Table 2).

The colorations of the two PVC formulations extruded testify to the effectiveness of the compositions containing organotin maleates obtained according to the present invention in preventing the heat degradation of PVC during the processing thereof. It is also shown that these compositions containing organotin maleates make it possible to retain a high Vicat point level, in accordance with the applicational requirements.

A dynamic thermal stability test is carried out on three other PVC formulations prepared like the PVC formulations 1 and 2.

The following designations are used:

PVC formulation 3, a formulation containing the composition containing organotin maleates of Example 5;

PVC formulation 4, a formulation containing the composition containing organotin maleates of Example 2;

PVC formulation 5, a formulation containing the composition containing organotin maleates of Example 6.

This dynamic thermal stability test makes it possible to demonstrate the remarkable stabilizing effect contributed by the compositions described, varying via the molar ratio of the species RA and R¹A of low and high molecular weight.

150 g of the PVC formulations 3, 4 and 5 are evaluated using a Collin roll mill, the rollers of which are brought to 200° C. The rotational speeds of the two cylinders are respectively adjusted to 20 rev/min and 24 rev/min, so as to gel and then squeeze the material between the cylinders while contributing frictional mechanical work. The separation between the cylinders is adjusted to 0.7 mm.

Samples are withdrawn from the cylinders at regular time intervals, their coloration being recorded, until complete degradation.

The yellowing indices (YI, ASTM Standard E313) measured on each sample withdrawn and the degradation time corresponding to complete darkening are presented in Table 4.

TABLE 4

|  | PVC formulation 3 | PVC formulation 4 | PVC formulation 5 |
|---|---|---|---|
| YI (2 min) | 5.7 | 5.4 | 4.8 |
| TI (4 min) | 8.4 | 7.4 | 7.3 |
| YI (6 min) | 10.0 | 8.9 | 9.1 |
| YI (8 min) | 11.8 | 10.0 | 10.2 |
| YI (10 min) | 13.4 | 11.5 | 11.9 |
| YI (12 min) | 15.2 | 13.0 | 12.7 |
| YI (15 min) | 18.5 | 15.7 | 15.3 |
| YI (20 min) | 27.3 | 23.4 | 21.3 |
| YI (25 min) | 33.9 | 32.3 | 30.5 |
| YI (30 min) | 38.6 | 37.0 | 36.1 |
| Complete degradation (min) | 45 | 45 | 50 |

III EVALUATION OF THE FINAL PROPERTIES OF RIGID PVC SECTIONS FORMED FROM PVC FORMULATIONS CONTAINING THE COMPOSITIONS CONTAINING ORGANOTIN MALEATES.

In order to demonstrate the final properties of rigid sections heat-stabilized by the compositions containing organotin maleates described in the invention, a rigid PVC formulation stabilized using lead salts has been extruded in the same way as the PVC formulation 4 and the PVC formulation 6 (PVC formulation containing the composition containing organotin maleates of Example 7). Lead salts form a stabilizing system, well known to a person skilled in the art, which represents a reference, the effectiveness of which is proved by its extensive use by converters of rigid sections.

To do this, a PVC formulation 7 is prepared according to the procedure used to prepare the PVC formulations 1 to 6, except that the 3.5 parts of composition containing organotin maleates are replaced with a combination of 3.5 parts of dibasic lead phosphite (2PbO·PbHPO$_3$·½H$_2$O) and 0.5 part of dibasic lead stearate (2PbO·Pb(OOCC$_{17}$H$_{35}$)$_2$).

A dynamic thermal stability test makes it possible to demonstrate the remarkable stabilizing effect contributed by the compositions described:

150 g of the PVC formulations 4, 6 and 7 are evaluated using a Collin roll mill according to the procedure described above (evaluation of the PVC formulations 3, 4 and 5, Table 4). The yellowing indices (YI, ASTM Standard E313) measured on each sample withdrawn are presented in Table 5.

TABLE 5

|  | PVC formlation 4 | PVC formulation 6 | PVC formulation 7 (reference) |
|---|---|---|---|
| YI (2 min) | 5.1 | 5.6 | 5.4 |
| YI (4 min) | 7.5 | 8.6 | 7.7 |
| YI (6 min) | 9.3 | 10.8 | 8.7 |
| YI (8 min) | 10.7 | 12.2 | 9.2 |
| YI (10 min) | 12.0 | 13.3 | 9.6 |
| YI (15 min) | 15.0 | 17.0 | 11.0 |

The three PVC formulations 4, 6 and 7 have also been converted on a Reifenhaüser BT65 industrial extruder equipped with a T-shaped die for window sections.

The parameters recorded during the extrusion are presented in Table 6.

TABLE 6

|  |  | PVC formulation 4 | PVC formulation 6 | PVC formulation 7 (reference) |
|---|---|---|---|---|
| Temperature profile (° C.) |  |  |  |  |
| In the barrel | zone 1 | 180 | 180 | 170 |
|  | zone 2 | 180 | 185 | 175 |
|  | zone 3 | 180 | 180 | 170 |
|  | zone 4 | 180 | 180 | 175 |
| in the die | zone 8 | 185 | 185 | 185 |
|  | zone 9 | 190 | 190 | 190 |
| Screw temperature (° C.) |  | 140 | 140 | 140 |
| Screw speed (rev/min) |  | 25 | 25 | 25 |
| Covering of the screws |  | yes | yes | yes |
| Bulk temperature (° C.) |  | 190 | 181 | 187 |
| Amperage |  | 7.3 | 5.7 | 7.5 |
| Throughput (kg/h) |  | 62.8 | 58.6 | 59.8 |

The parameters recorded during extrusion show that the behaviour of the PVC formulation 4 (containing the composition of Example 2 obtained with Unilin® 425) is very similar to that of the PVC formulation 7 (containing the stabilization system with lead).

On the other hand, the PVC formulation 6 (containing the composition of Example 7 obtained with Unilin® 550) has a significantly different Theological behaviour, once again demonstrating the lubricating effect of high molecular weight alcohols. This formulation would require the lubrication to be optimized in order to produce rheological behaviour similar to that of the PVC formulation 7 containing lead.

The sections extruded from the PVC formulations 4 and 7 were evaluated and the results are presented in Table 7.

TABLE 7

|  | PVC formulation 4 | PVC formulation 7 (reference) |
|---|---|---|
| Coloration of sections |  |  |
| L* | 93.8 | 94.8 |
| a* | −0.43 | −0.36 |
| b* | 2.85 | 2.26 |
| 60° Gloss | 24.6 | 15.7 |
| Residual stability (min) (Congo Red) | 38 | 60 |
| Softening temperature (° C.) (Vicat Point) | 79.7 | 80.3 |

The mechanical properties of the sections were evaluated by measuring the Charpy impact resilience according to DIN Standard 53753, used in Germany for the evaluation of rigid sections for external joinery. The results are presented in Table 8.

TABLE 8

|  | PVC formulation 4 | PVC formulation 7 (reference) |
|---|---|---|
| Resilience <R> in kJ/m$^2$ | 60.5 | 62.6 |

The effectiveness of the compositions containing organotin maleates described in the invention as heat-stabilizer during the processing on industrial equipment of opaque rigid PVC formulations intended for the manufacture of extruded sections is thus demonstrated.

Indeed, they make it possible to ensure easy processing of the formulations, as is shown by the extrusion parameters of the PVC formulation 4, which are very similar to those obtained for a reference formulation stabilized with lead salts, in particular as regards the amperage of the motor for driving the screws and the throughput of the extruder.

The colorations of the sections obtained with the PVC formulation 4, which are similar to those observed with the reference formulation containing lead, show the effectiveness of the compounds based on organotin maleates in heat-stabilizing the formulations and thus reducing the heat degradation of PVC during the processing thereof.

Finally, it is noted that the Charpy impact resilience value obtained for the sections stabilized with the composition based on organotin maleates (PVC formulation 4) is greater than the value of 50 kJ/m$^2$ recommended by DIN Standard 53753.

The preceding examples can be repeated with similar success by substituting the generically or specifically described reactants and/or operating conditions of this invention for those used in the preceding examples.

The entire disclosure of all applications, patents and publications, cited above, and of corresponding French application 97/00147, are hereby incorporated by reference.

From the foregoing description, one skilled in the art can easily ascertain the essential characteristics of this invention, and without departing from the spirit and scope thereof can make various changes and modifications of the invention to adapt it to various usages and conditions.

What is claimed is:

1. A composition containing organotin maleates as obtained by the reaction of a mixture composed of at least one component RA and at least one component R$^1$A with maleic anhydride and then bringing the reaction mixture thus obtained into reactive contact with at least one dialkyltin oxide (R$^2$)$_2$Sn=O, or with at least one alkyltin chloride (R$^2$)$_x$SnCl$_{4-x}$ wherein:

RA represents
either an alcohol ROH in which R represents a linear or branched aliphatic hydrocarbon radical having a number of carbon atoms of 1 to 10 or a mixture of alcohols with a weight-average molecular mass $\overline{Mw}$ greater than 32 and not more than 158,
or an epoxyalkane C$_n$H$_{2n}$O in which n is 1 to 10 or a mixture of epoxyalkanes with a weight-average molecular mass $\overline{Mw}$ greater than 30 and not more than 156;

R$^1$A represents
either an alcohol R$^1$OH in which R$^1$ represents a linear or branched aliphatic hydrocarbon radical having a number of carbon atoms of 20 to 50 or a mixture of saturated primary alcohols with a weight-average molecular mass $\overline{Mw}$ of 298 to 718,
or an epoxyalkane C$_p$H$_{2p}$O in which p is 20 to 50 or a mixture of epoxyalkanes with a weight-average molecular mass $\overline{Mw}$ of 296 to 716;

R$^2$ represents a linear or branched aliphatic hydrocarbon radical having a number of carbon atoms of 1 to 12,
x is an integer equal to 1 or 2.

2. A composition according to claim 1, characterized in that the reaction takes place in the presence of a solvent.

3. A composition according to claim 2, prepared according to the following stages: producing a mixture of the components RA and R$^1$A in solvent medium while heating, then adding to the mixture thus obtained, which has been brought to a temperature of at least 50° C., maleic anhydride over a period of time ranging from 15 minutes to 1 hour, and then subsequently adding a dialkyltin oxide (R$^2$)$_2$Sn=O over a period of time ranging from 15 minutes to 90 minutes; heating the reaction mixture thus obtained at a temperature ranging from 50° C. to 120° C. for a period of time ranging from 15 minutes to 90 minutes and removing the water formed and the solvent under reduced pressure at a temperature ranging from 70° C. to 120° C.

4. A composition according to claim 1 having a maleic anhydride/(RA+R$^1$A) molar ratio of at least 1.5.

5. A composition according to claim 1, having a RA/R$^1$A molar ratio from 1/99 to 99/1.

6. A composition according to claim 1 characterized in that at least 0.50 mol of dialkyltin oxide (R$^2$)$_2$Sn=O is used per 1 mol of maleic anhydride.

7. A composition according to claim 1 characterized in that the compound RA is the alcohol ROH.

8. A composition according to claim 7, characterized in that the alcohol ROH is 2-ethylhexanol.

9. A composition according to claim 1 characterized in that the compound R$^1$A is a mixture of saturated primary alcohols having a weight-average molecular mass $\overline{Mw}$ ranging from 375 to 700.

10. A composition according to claim 1 characterized in that the compound R$^1$A is a mixture of epoxyalkanes C$_p$H$_{2p}$O having a weight-average molecular mass $\overline{Mw}$ ranging from 313 to 632.

11. A composition according to claim 1 characterized in that the dialkyltin oxide is dibutyltin oxide.

12. A composition according to claim 1, wherein the reaction mixture is contacted with a mixture of monoalkyltin trichloride R$^2$SnCl$_3$ and of dialkyltin dichloride (R$^2$)$_2$SnCl$_2$.

13. A composition according to claim 1, characterized in that the reactive contact takes place in the presence of water.

14. A composition according to claim 1, characterized in that the reactive contact is conducted in the presence of a costabilizer.

15. A composition according to claim 14, characterized in that the costabilizer is a zeolite.

16. A process for producing a composition containing organotin maleates, wherein a mixture composed of at least one component RA and at least one component R$^1$A is reacted with maleic anhydride and that the reaction mixture thus obtained is then brought into reactor contact with at least one dialkyltin oxide (R$^2$)$_2$Sn=O, or with at least one alkyltin chloride (R$^2$)$_x$SnCl$_{4-x}$ wherein:

RA represents
either an alcohol ROH in which R represents a linear or branched aliphatic hydrocarbon radical having a number of carbon atoms of 1 to 10 or a mixture of alcohols with a weight-average molecular mass $\overline{Mw}$ greater than 32 and not more than 158,
or an epoxyalkane C$_n$H$_{2n}$O in which n is 1 to 10 or a mixture of epoxyalkanes with a weight-average molecular mass $\overline{Mw}$ greater than 30 and not more than 156;

R¹A represents
either an alcohol R¹OH in which R¹ represents a linear or branched aliphatic hydrocarbon radical having a number of carbon atoms of 20 to 50 or a mixture of saturated primary alcohols with a weight-average molecular mass $\overline{Mw}$ of 298 to 718,
or an epoxyalkane $C_pH_{2p}O$ in which p is 20 to 50 or a mixture of epoxyalkanes with a weight-average molecular mass $\overline{Mw}$ of 296 to 716;

$R^2$ represents a linear or branched aliphatic hydrocarbon radical having a number of carbon atoms of 1 to 12, x is an integer equal to 1 or 2.

17. A process according to claim 16, characterized in that the operation is carried out in solvent medium.

18. A process according to claim 17, characterized in that a mixture of the components RA and R¹A is prepared in solvent medium while heating, that maleic anhydride is then added over a period of time ranging from 15 minutes to 1 hour to the mixture thus obtained, which has been brought to a temperature of at least 50° C., and that a dialkyltin oxide $(R^2)_2Sn=O$ is then subsequently added over a period of time ranging from 15 minutes to 90 minutes; that the reaction mixture thus obtained is heated at a temperature ranging from 50° C. to 120° C. for a period of time ranging from 15 minutes to 90 minutes and that the water formed and the solvent are removed under reduced pressure at a temperature ranging from 70° C. to 120° C.

19. A process according to claim 16, characterized in that the maleic anhydride/(RA+R¹A) molar ratio is at least 1.5.

20. A process according to claim 16, characterized in that the ratio of the molar percentages RA/R¹A ranges from 1/99 to 99/1.

21. A process according to claim 16, characterized in that at least 0.50 mol of dialkyltin oxide $(R^2)_2Sn=O$ is used per 1 mol of maleic anhydride.

22. A process according to claim 16, characterized in that the compound RA is the alcohol ROH.

23. A process according to claim 22, characterized in that the alcohol ROH is 2-ethylhexanol.

24. A process according to claim 16, characterized in that the compound R¹A is a mixture of saturated primary alcohols having a weight-average molecular mass $\overline{Mw}$ ranging from 375 to 700 and a polydispersity $\overline{Mw}/\overline{Mn}$ in the region of 1.

25. A process according to claim 16, characterized in that the compound R¹A is a mixture of epoxyalkanes $C_pH_{2p}O$ having a weight-average molecular mass $\overline{Mw}$ ranging from 313 to 632.

26. A process according to claim 16 to, characterized in that the dialkyltin oxide is dibutyltin oxide.

27. A process according to claim 16, characterized in that the operation is carried out with a mixture of monoalkyltin trichloride $R^2SnCl_3$ and of dialkyltin dichloride $(R^2)_2SnCl_2$.

28. A process according to claim 16 to, characterized in that the operation is carried out in the presence of water.

29. A process according to claim 16 to, characterized in that the operation is carried out in the presence of a costabilizer.

30. A process according to claim 29, characterized in that the costabilizer is a zeolite.

31. A stabilized and lubricated thermoplastic polymer composition including a composition containing organotin maleates according to claim 1.

32. A composition according to claim 31, characterized in that the thermoplastic polymer is a homo- or copolymer of vinyl chloride.

33. A compact extruded rigid article, characterized in that it is formed from a thermoplastic polymer composition according to claim 31.

34. A composition according to claim 1, wherein RA has between 5 and 8 carbon atoms.

35. A composition according to claim 1, wherein $R^2$ has 1, 4 or 8 carbon atoms.

36. A composition according to claim 3, wherein a mixture of the components RA and R¹A in a solvent medium is heated to between 70° C. and 100° C. while maleic anhydride is added thereto, the reaction mixture obtained by the addition of dialkyltin oxide to the mixture of RA, $R^{1A}$ and maleic anhydride is heated to between 75° C. and 100° C., and the solvent and water are removed under reduced pressure at a temperature between 80° C. and 100° C.

37. A composition according to claim 4, wherein said molar ratio is between 2 and 2.5.

38. A composition according to claim 5, wherein said molar ratio is between 20/80 and 80/20.

39. A composition according to claim 6, wherein the amount of dialkyltin oxide is used in an amount ranging from 0.75 mole to 0.85 mole per mole of maleic anhydride.

40. A composition according to claim 9, wherein said mixture of alcohols has a mass $\overline{Mw}$ of 460 or 550.

41. A composition according to claim 10, wherein said mixture of epoxyalkanes has a mass $\overline{Mw}$ of 632.

42. A composition according to claim 1, wherein compound R¹A comprises saturated primary alcohol having a weight-average molecular mass $\overline{Mw}$ ranging from 375 to 700; or the compound R¹A comprises epoxyalkane having a weight-average molecular mass $\overline{Mw}$ ranging from 313 to 632; or mixtures of said saturated primary alcohol and said epoxyalkane.

43. A composition according to claim 42, wherein the mass $\overline{Mw}$ of the saturated primary alcohol is 460 or 550 and the mass $\overline{Mw}$ of epoxyalkane is 632.

44. A mixture of organotin maleates comprising:
(a) an organotin maleate produced from RA, which represents
either ROH in which R represents a linear or branched aliphatic hydrocarbon radical having a number of carbon atoms ranging from 1 to 10 or a mixture of alcohols with a weight-average molecular mass $\overline{Mw}$ greater than 32 and not more than 158,
or an epoxyalkane $C_nH_{2n}O$ in which n is 1 to 10 or a mixture of epoxyalkanes with a weight-average molecular mass $\overline{Mw}$ greater than 30 and not more than 156; and
(b) organotin maleates produced from R¹A, wherein R¹A represents
either R¹OH in which R¹ represents a linear or branched aliphatic hydrocarbon radical having a number of carbon atoms of 20 to 50 or a mixture of saturated primary alcohols with a weight-average molecular mass $\overline{Mw}$ of 298 to 718,
or an epoxyalkane $C_pH_{2p}O$ in which p is 20 to 50 or a mixture of epoxyalkanes with a weight-average molecular mass $\overline{Mw}$ of 296 to 716.

45. A composition according to claim 44, wherein R¹A comprises saturated primary alcohol having a weight-average molecular mass $\overline{Mw}$ ranging from 375 to 700; or R¹A comprises epoxyalkane having a weight-average molecular mass $\overline{Mw}$ ranging from 313 to 632; or mixtures of said saturated primary alcohol or said epoxyalkane.

46. A composition containing organotin maleates as obtained by the reaction of a mixture composed of at least one component RA and at least one component R¹A in a molar ratio RA/R¹A of 1/99 to 99/1 with maleic anhydride at a ratio of maleic anhydride/(RA+R¹A) of at least 1.5, and then bringing the reaction mixture thus obtained into contact with at least one dialkyltin oxide $(R^2)_xSnCl_{4-x}$, wherein:

RA represents
- either an alcohol ROH in which R represents a linear or branched aliphatic hydrocarbon radical having a number of carbon atoms ranging from 1 to 10 or a mixture of alcohols with a weight-average molecular mass $\overline{Mw}$ greater than 32 and not more than 158,
- or an epoxyalkane $C_nH_{2n}O$ in which n is 1 to 10 or a mixture of epoxyalkanes with a weight-average molecular mass $\overline{Mw}$ greater than 30 and not more than 156;

$R^1A$ represents
- either an alcohol $R^1OH$ in which $R^1$ represents a linear or branched aliphatic hydrocarbon radical having a number of carbon atoms of 20 to 50 or a mixture of saturated primary alcohols with a weight-average molecular mass $\overline{Mw}$ of 298 to 718,
- or an epoxyalkane $C_pH_{2p}O$ in which p is 20 to 50 or a mixture of epoxyalkanes with a weight-average molecular mass $\overline{Mw}$ of 296 to 716;

$R^2$ represents a linear or branched aliphatic hydrocarbon radical having a number of carbon atoms of 1 to 12, x is an integer equal to 1 or 2.

47. A composition according to claim 46, wherein at least 0.50 mol of dialkyltin oxide $(R^2)_2Sn=O$ is used per 1 mol of maleic anhydride.

48. A process for producing a composition containing organotin maleates wherein a mixture composed of at least one component RA and at least one component $R^1A$ in a molar ratio $RA/R^1A$ of 1/99 to 99/1 with maleic anhydride at a ratio of maleic anhydride/$(RA+R^1A)$ of at least 1.5, and that the reaction mixture thus obtained is then brought into reactor contact with at least one dialkyltin oxide $(R^2)_2Sn=O$, or with at least one alkyltin chloride $(R^2)_xSnCl_{4-x}$ wherein:

RA represents
- either an alcohol ROH in which R represents a linear or branched aliphatic hydrocarbon radical having a number of carbon atoms of 1 to 10 or a mixture of alcohols with a weight-average molecular mass $\overline{Mw}$ greater than 32 and not more than 158,
- or an epoxyalkane $C_nH_{2n}O$ in which n is 1 to 10 or a mixture of epoxyalkanes with a weight-average molecular mass $\overline{Mw}$ greater than 30 and not more than 156;

$R^1A$ represents
- either an alcohol $R^1OH$ in which $R^1$ represents a linear or branched aliphatic hydrocarbon radical having a number of carbon atoms of 20 to 50 or a mixture of saturated primary alcohols with a weight-average molecular mass $\overline{Mw}$ of 298 to 718,
- or an epoxyalkane $C_pH_{2p}O$ in which p is 20 to 50 or a mixture of epoxyalkanes with a weight-average molecular mass $\overline{Mw}$ of 296 to 716;

$R^2$ represents a linear or branched aliphatic hydrocarbon radical having a number of carbon atoms of 1 to 12, x is an integer equal to 1 or 2.

49. A process according to claim 48, wherein at least 0.50 mol of dialkyltin oxide $(R^2)_2Sn=O$ is used per 1 mol of maleic anhydride.

50. A mixture of organotin maleates comprising
(a) an organotin maleate produced from RA, which represents
- either ROH in which R represents a linear or branched aliphatic hydrocarbon radical having a number of carbon atoms of 1 to 10 or a mixture of alcohols with a weight-average molecular mass $\overline{Mw}$ greater than 32 and not more than 158,
- or an epoxyalkane $C_nH_{2n}O$ in which n is 1 to 10 or a mixture of epoxyalkanes with a weight-average molecular mass $\overline{Mw}$ greater than 30 and not more than 156; and (b) organotin maleates produced from $R^1A$, wherein $R^1A$ represents
- either $R^1OH$ in which $R^1$ represents a linear or branched aliphatic hydrocarbon radical having a number of carbon atoms of 20 to 50 or a mixture of saturated primary alcohols with a weight-average molecular mass $\overline{Mw}$ of 298 to 718,
- or an epoxyalkane $C_pH_{2p}O$ in which p is 20 to 50 or a mixture of epoxyalkanes with a weight-average molecular mass $\overline{Mw}$ of 296 to 716 wherein the molar ratio $RA/R^1A$ is 1/99 to 99/1.

51. A mixture according to claim 50, produced from a mixture of maleic anhydride, RA and $R^1A$ at a ratio of maleic anhydride/ $(RA+R^1A) \geq 1.5$.

* * * * *